(12) United States Patent
Engelbrecht et al.

(10) Patent No.: US 6,403,751 B1
(45) Date of Patent: Jun. 11, 2002

(54) ADHESION PROMOTERS FOR SILICONE MATERIALS

(75) Inventors: Jürgen Engelbrecht; Martin Kix, both of Elmshorn (DE)

(73) Assignee: S & C Polymer, Elmshorn (DE)

( * ) Notice: Subject to any disclaimer, the term of this patent is extended or adjusted under 35 U.S.C. 154(b) by 0 days.

(21) Appl. No.: 09/455,718

(22) Filed: Dec. 7, 1999

(30) Foreign Application Priority Data

Apr. 7, 1999 (DE) .......................................... 199 15 492

(51) Int. Cl.$^7$ ............................................... C08G 77/04

(52) U.S. Cl. ..................................................... 528/25

(58) Field of Search ............................................ 528/25

(56) References Cited

U.S. PATENT DOCUMENTS

| | | | | |
|---|---|---|---|---|
| 4,083,856 A | * | 4/1978 | Mendicino | 260/348.12 |
| 4,101,492 A | * | 7/1978 | Lindemann | 260/29.6 |
| 4,218,294 A | * | 8/1980 | Brack | 204/159.13 |
| 4,463,127 A | * | 7/1984 | Alberts | 524/731 |
| 5,057,358 A | * | 10/1991 | Riding | 428/209 |
| 5,118,559 A | * | 6/1992 | DeVoe | 428/262 |
| 5,397,813 A | * | 3/1995 | Eckberg | 522/31 |
| 5,650,453 A | * | 7/1997 | Eckberg | 522/31 |
| 5,721,290 A | * | 2/1998 | Eckberg | 522/31 |
| 5,814,679 A | * | 9/1998 | Eckberg | 522/31 |
| 5,891,966 A | * | 4/1999 | Murray | 525/342 |

\* cited by examiner

*Primary Examiner*—Paul R. Michl
(74) *Attorney, Agent, or Firm*—Frommer Lawrence & Haug, LLP; Ronald Santucci

(57) ABSTRACT

There are disclosed according to the invention copolymers having repeating structural units a) of the formula

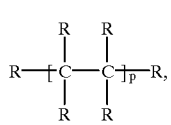

(I)

and b) of the formula (II)

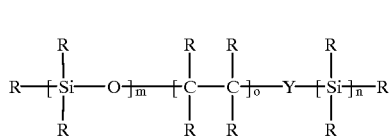

(II)

wherein m and p are each independently of the other whole numbers>0, n=1, o=1 or 0, Y is a bond or a group of the formula —$CR_2$— or —CO—O—$CR_2$—$CR_2$—$CR_2$—, each of the radicals R independently of the others is a H atom, an alkyl group, a group of the formula —$CR'_2$—OR', —OR', —COOR', —$SiR_cR_dR_e$, or —$NR_d$—$R_c$, an organic acid radical, its anhydride or its corresponding readily hydrolysable ester of the formula —O—CO—$R_c$ or its corresponding readily hydrolysable amide of the formula —$NR_d$—CO—$R_c$, a phenyl group optionally substituted by one or two —CR'=CR'$_2$ groups, or a group of the formula —$CR_eR_f$CHR$_g$—$SiX_3$, a group of the formula —SiOSiO(SiO)$_m$H, an epoxy group, an aziridine group, a phosphate or phosphorate group or an anhydride thereof or a bond, or two radicals R together represent a group of the formula =CR2, and each of the radicals R', $R_c$, $R_d$, $R_e$, $R_f$, $R_g$ and X independently of the others may be a H atom, a OH group, an alkyl group, an alkoxy group or an aryl group, with the proviso that in at least one unit of the formula II at least one radical R bonded to a Si atom is a —OH, —$OR_c$ or —$NR_dR_c$ group or a radical of the formula —OCOR$_c$ or —$NR_d$COR$_c$.

25 Claims, No Drawings

ADHESION PROMOTERS FOR SILICONE MATERIALS

TECHNICAL FIELD

The invention relates to copolymers of hydrogen siloxanes and unsaturated compounds. More specifically, the present invention relates to copolymers of hydrogen siloxanes and unsaturated compounds, wherein at least some of the SiH groups have been converted into silanol groups or reactive derivatives thereof and/or at least some of the SiH groups have silanol groups or reactive derivatives thereof bonded to them. The instant invention also relates to adhesive solutions made from said copolymers, to the use of said copolymers to promote adhesion between condensation-crosslinking silicone relining compositions and prostheses. Finally, the instant invention relates to the use of said copolymers to promote the adhesion of condensation-crosslinking silicone impression compositions to impression trays, and to other uses.

BACKGROUND ART

Materials for dental prostheses generally consist of polymethylmethacrylate or of copolymers of different methacrylates. When a prosthesis no longer fits well, it must be manufactured afresh or relined (corrected). This relining may be effected with prosthesis material again (a hard relining) but it may also be necessary to choose a significantly softer material for such purposes (a non-hardening relining). With the average age increasing, there is a considerable rise in the demand for the last-mentioned soft materials.

Customary soft relining materials consist of polymethacrylates to which plasticiser has been added or of silicone. The polymethacrylates to which plasticiser has been added can be polymerised onto the (polymethylmethacrylate) prosthesis material, but in the course of a few months become harder to the point of brittleness as a result of the plasticiser's dissolving out. Relinings with silicone elastomers do not exhibit such brittleness. They lemain soft over a prolonged period, but on the other hand the provision of a firm bond between silicone elastomers and polymethacrylates always presents a considerable problem. Even when attempts are made to join the layers mechanically by etching or mechanical roughening, the silicone layer becomes detached from the prosthesis after a few weeks or even after a few days.

Several methods of solving this problem by chemical means have been described. For example, DE 196 35 696 A1 describes polymers containing reactive groups, such as —OH or —NH, to which hydrogen silicone units are linked, with hydrogen being removed. Solutions of such SiH-group-containing copolymers, after being applied to the surface of a prosthesis, are able to react with and become bonded to an addition-crosslinking vinyl silicone layer applied thereto. Since the hydrogen siloxane units are linked via —C—O—Si— bonds or via —C—NH—Si— bonds, adhesive bonds made in accordance with this Offenlegungsschrift are extremely hydrolysis-labile in the aqueous environment of the mouth and are suitable only for short-term temporary relinings of a few days or weeks.

A better solution to the problem is described in EP 0 632 060 A1 which describes for such purposes copolymers that are prepared by copolymerisation of methacrylates with vinyl- or allyl-methacrylates, hydrogen silicones having an adequate SiH content then being linked to free vinyl or allyl groups with the aid of a platinum catalyst.

Solutions of such SiH-group-containing copolymers, after being applied to the surface of a prosthesis, are likewise able to react with and become bonded to a vinyl silicone layer applied thereto. The hydrogen siloxane units are linked to the polymer chain structures via ester groups —CO—O—, have better resistance to hydrolysis and are therefore effective over a longer period of time as promoters of adhesion between the material of the prosthesis and the applied silicone, even in the aqueous environment of the mouth. The preparation process is a multiple-step procedure and is therefore inconvenient and expensive and the polymers prepared have acid-and base-sensitive ester groups.

The accompanying patent application DE 199 05 224.7 describes as a better solution very hydrolysis-resistant SiH-group-containing copolymers that have proved to be very effective adhesion promoters for the relining of prostheses with addition-crosslinking silicones and additionally also have excellent properties when they are used as impression tray adhesives for addition-crosslinking silicone impression materials.

The above-mentioned adhesives of patent specification EP 0 632 060 A1 and the more advanced adhesives of patent application DE 199 05 224.7 have proved satisfactory as adhesives with potentially high adhesive strengths. They can be used effectively, however, only for the adhesive bonding of addition-crosslinking vinyl silicones.

Similar questions and problems also apply, however, to a broad product range of condensation-crosslinking silicones. Here too it would be desirable to find similarly effective adhesive bonding systems.

SUMMARY OF THE INVENTION

The invention is a new type of hydrolysis-resistant materials that, especially when used in the form of a solution, result in lastingly stable, moisture-resistant adhesion behavior between prosthesis material and non-hardening condensation-crosslinking silicone relining and also optionally between the material of an impression tray and the condensation-crosslinking silicone impression material.

In other words, the invention provides materials that, especially when used in the form of a solution, bring about a strong adhesive action between prosthesis material and condensation-crosslinking silicones and that are able to act as lastingly stable, moisture-resistant adhesives between prosthesis material and non-hardening silicone relinings of condensation-crosslinking silicones and also as strong impression tray adhesives for condensation-crosslinking silicone impression materials.

DISCLOSURE OF THE INVENTION

There are disclosed according to the invention copolymers having repeating structural units a) of the formula (I)

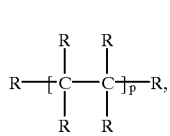

and b) of the formula (II)

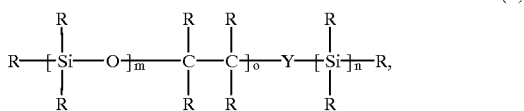

In the preceding formulae m and p are each, independently of the one another, whole numbers >0; n=1; o=1 or 0; Y is a bond or a group of the formula —$CR_2$— or —CO—O—$CR_2$—$CR_2$—$CR_2$—; each of the radicals R, independently of one another, is a hydrogen atom, an alkyl group, a group of the formula —$CR'_2$—OR', —OR', —COOR', —$SiR_c$,$R_d$, $R_e$, —$NR_d$—$R_c$, an organic acid radical, its anhydride or its corresponding readily hydrolysable ester of the formula —O—CO—$R_c$ or its corresponding readily hydrolysable amide of the formula —$NR_d$—CO—$R_c$, a phenyl group optionally substituted by one or two —CR'=$CR'_2$ groups, or a group of the formula —$CR_e$,$R_f$CHR$_g$—$SiX_3$, a group of the formula —SiOSiO(SiO)$_m$H, an epoxy group, an aziridine group, a phosphate or phosphorate group or an anhydride thereof or a bond, or two radicals R together represent a group of the formula =CR2; and each of the radicals R', $R_c$, $R_d$, $R_e$, $R_f$, $R_g$ and X independently of the others may be a hydrogen atom, an OH group, an alkyl group, an alkoxy group or an aryl group; with the proviso that in at least one unit of the formula II at least one radical R bonded to a Si atom is a —OH, —$OR_c$, or —$NR_d R_c$ group or a radical of the formula —$OCOR_c$, or —$NR_d COR_c$.

Preferably the radicals R, $R_c$, $R_d$, $R_e$, $R_f$, $R_g$ and X are independently of one another, H atoms, OH, methyl, ethyl, methoxy or ethoxy groups. Preferably at least one unit of the formula I and one unit of the formula II are linked to one another via C—Si bonds and/or via —OCO— bonds.

The alkyl groups mentioned are substituted or unsubstituted, branched or unbranched and have preferably from 1 to 12, more preferably from 1 to 6 and most preferably 1, 2 or 3 carbon atoms. The aryl groups mentioned are substituted or unsubstituted and have 1, 2, 3 or 4 condensed aromatic rings. As substituents there are defined according to the invention e.g. branched or unbranched groups having 1, 2, 3 or 4 carbon atoms, —$NO_2$, —CN, —$NH_2$, —COOH, vinyl, allyl or —$CONH_2$ groups.

According to the invention the ratio of silanol-siloxane fragments of the formula II to fragments of the formula I in the copolymer is preferably at least 1:25, more preferably at least 1:10 and most preferably 1:5.

According to the invention, furthermore, an adhesive is prepared that comprises at least one copolymer according to the invention and preferably a readily volatile solvent.

For the preparation of the copolymers according to the invention it is possible in a first step to prepare hydrogen siloxane copolymers. This is effected, for example, by copolymerisation of unsaturated compounds with SiH-group-containing siloxanes as disclosed in DE 199 05 224.7, where the hydrogen siloxane group is bonded via C—Si bonds to or in the polymer chain, or by preparation of hydrogen siloxane copolymers, as disclosed in EP 0 632 060 A1, in which the hydrogen siloxane groups are bonded indirectly to the polymer chain via ester groups —OCO—.

There may be copolymerised, for example, monomers of unsaturated compounds and monomers of SiH-group-containing siloxanes, homo- and/or co-polymers of unsaturated compounds with monomers of SiH-group-containing siloxanes, monomers of unsaturated compounds with homo- and/or co-polymers of SiH-group-containing siloxanes, or homo- and/or co-polymers of unsaturated compounds with homo- and/or co-polymers of SiH-group-containing siloxanes.

In a second step, according to the invention some or all of the SiH groups may be converted into silanol groups or reactive derivatives thereof, for example by hydrolysis, alcoholysis, acidolysis or similar reactions, for example with hydrogen removal and optionally with platinum catalysis:

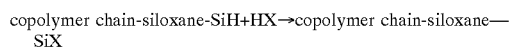

wherein X may be at least one of the following radicals or groups: —OH, —$OR_c$, —$NR_d$—$R_c$, readily hydrolysable esters or amides of the formula —O—CO—$R_c$, or —$NR_d$—CO—$R_c$, wherein $R_c$, $R_d$ alkyl or aryl. As intermediates it is also possible to prepare polymers in which X is at least one halogen. Those polymers should, however, be converted into the more stable and more compatible derivatives defined above, since they can be used more compatibly.

HX may, however, also be silicones having SiOH groups:

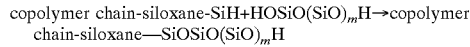

The unsaturated compounds may be, for example, meth (acrylates), vinyl benzenes, vinyl ethers, allyl compounds, vinyl silanes or derivatives or mixtures thereof and especially mono(meth)-monovinyl benzenes, monovinyl ethers, monoallyl compounds, monovinyl silanes or derivatives or mixtures thereof.

In a preferred embodiment, the unsaturated compounds contain at least one further functional group, such as hydrogen silyl, alkoxysilyl, epoxy or aziridine groups, carboxylic acid or carboxylic acid anhydride groups, phosphate or phosphorate groups and anhydrides thereof.

In accordance with an alternative, in a different second step via a hydrosilylation reaction, unsaturated silanol derivatives having, for example, the formula $R_e$,$R_f$C=$CR_g SiX_3$ may be added to the SiH groups of the hydrogen siloxane copolymer and thus converted into a copolymer having silanol groups or derivatives thereof; in those cases the reaction proceeds without hydrogen removal, by addition alone, which is optionally platinum catalysed:

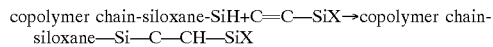

As unsaturated silanol derivatives there are suitable, for example, vinyl triethoxysilane, allyl dimethylmethoxysilane or methacrylpropyl triethoxysilane. The silanol-siloxane units (SiX-siloxane) are bonded to the chain of polymerised double bonds by either lateral or terminal linkages,

but they may also, linked on two or more sides as siloxane units, be an integral part of the chain structure:

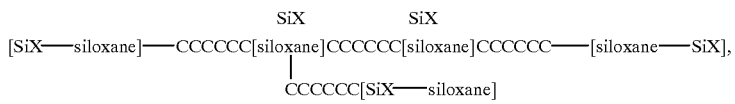

or mixtures of all types.

Copolymers according to the invention may therefore also be prepared by copolymerising at least one compound of the formula I or a compound having repeating units of the formula I with a compound of the formula II or a compound having repeating units of the formula II.

Apart from being determined by the nature and type of the functions R and/or X of the silanol group, the properties of the copolymers according to the invention and solutions thereof are determined to a great extent by the starting hydrogen silicone units used, in which the number of SiH groups and the ratios of neutral chain components to hydrogen siloxane chain components contribute to determining solubility and activity. In the case of the uses according to the invention as adhesives, the neutral chain components are, for example, important in order that they mix intimately in microregions with plastics to be partially dissolved and to be bonded or, when functional groups of that "neutral" chain of the formula I are present in a sufficient manner, in order that they exhibit functionality (such as, for example, adhesion in the case of phosphate groups), while on the other hand a large number of silanol-siloxane groups promotes good binding into a condensation-crosslinking silicone applied thereto. The ratio of silanol-siloxane components to non-siloxane components in the copolymer should in advantageous embodiments be at least 1:25, in preferred embodiments at least 1:10 and in especially preferred embodiments at least 1:5.

Adhesive solutions comprising the silanol-siloxane copolymers according to the invention have proved to be excellent adhesion promoters promoting adhesion between condensation-crosslinking silicone relining compositions and prostheses, and as adhesion promoters for promoting the adhesion of condensation-crosslinking silicone impression compositions to impression trays and also as excellent adhesives for other uses in connection with the adhesive bonding of silicones of the condensation-crosslinking type.

Suitable solvents for adhesive solutions according to the invention are especially readily volatile, inert solvents, such as halogenated or non-halogenated aliphatic or aromatic hydrocarbons, ethers, ketones, esters or cyclic siloxanes.

It may also be useful to mix into the adhesive solutions small amounts of catalysts, as are customary for condensation-crosslinking silicones, optionally also as an extra component that is mixed in only shortly before use.

Customary catalysts for condensation-crosslinking silicones are, for example, strong acids, such as $CF_3SO_3H$, or strong bases, such as $(CH_3)_4NOH$, or milder systems, such as amines, amine salts of organic acids and also organometal compounds of tin, titanium or zirconium, such as, for example, dibutyltin dilaurate, dibutyltin oxide or tetraalkoxytitanate. It is also possible to add as an ingredient silicon compounds that act as crosslinkers for condensation-crosslinking systems, such as tetraethyl silicate or oligosilicates thereof.

The copolymers according to the invention may also be used according to the invention for purposes other than those indicated. For example, the copolymers according to the invention can also be used e.g. as additives for improved crosslinking in condensation-crosslinking silicone mixtures or alternatively as starting components for the manufacture of copolymers further modified by further grafting, in which the silanol groups or other reactive groups also incorporated by polymerisation act as linkage points for grafting on other functional groups.

The copolymers according to the invention are suitable also as coatings that are crosslinkable on the supply of moisture, with hydrolysis taking place.

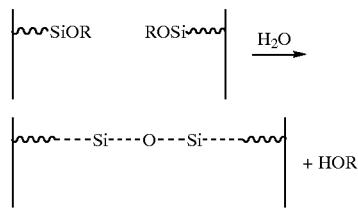

Such coatings exhibit excellent adhesion to noble and non-noble metals, glass, silicates, teeths and ceramics; if phosphate or carboxylic acid groups are present in the base chain, the coatings adhere especially well to non-noble metals and dental substrates.

The invention relates also to those uses.

The invention will be explained in more detail with reference to the following embodiments given by way of example.

EXAMPLE 1

Preparation of a Starting Hydrogen Siloxane Copolymer

For the preparation of a hydrogen siloxane copolymer, 0.3 g of benzoyl peroxide is added to a solution of 20 g of ethylmethacrylate, 40 g of polyfunctional hydrogen siloxane (crosslinker 430 from Bayer AG) and 40 g of toluene. The solution is heated at 90° C. for 2 hours. After cooling to room temperature, the toluene is evaporated off under reduced pressure and the residue that remains is washed free of crosslinker with a mixture of ethanol/methanol 1:1. A gel-like hydrogen siloxane copolymer is obtained.

For the preparation of a comparison adhesive solution as adhesive for addition-crosslinking silicones, 10 parts of the resulting polymer are dissolved in 90 parts of acetone. The adhesive solution is applied in a thin layer to a commercially available plastics impression tray of polycarbonate (Miratray —140°, Hager & Werken, Germany) and allowed to dry for 1 min. The tray is then charged with addition-crosslinking impression silicone and placed in the mouth in such a manner that the composition is as far as possible not pressed into the retaining holes. When the hardening period has elapsed, the tray is removed from the mouth and the slight retaining tongues that have formed are removed. The impression composition is so securely bonded to the impression tray, even without mechanical retaining means, that it can be removed from the impression tray again only by destruction. Attempts to use the tray in the same manner for an adhesive charge with condensation-crosslinking silicone are unsuccessful. The condensation-crosslinking impression composition is easily lifted away from the impression tray.

EXAMPLE 2

Preparation of a Silanol-siloxane Copolymer According to the Invention 3 g of the adhesive solution from Example 1 are diluted with 10 g of acetone and then 0.85 g of vinyl triethoxysilane is added. 0.01 g of a platinum catalyst (Silopren U catalyst Pt-S, GE Bayer, Netherlands) is added to the solution. The hydrosilylation reaction is monitored by means of the IR spectrum (SiH at 2158 cm$^{-1}$) and approximately a further 0.12 g of vinyl triethoxysilane is added until the SiH band has disappeared.

The triethoxysilanol-siloxane adhesive solution so prepared is applied in a thin layer using a brush to a commercially available plastics impression tray of polycarbonate (Miratray —140°, Hager & Werken, Germany) and allowed to dry for 1 min. The tray is then charged with condensation-crosslinking impression silicone and again placed in the mouth in such a manner that the composition is as far as possible not pressed into the retaining holes and when the hardening period has elapsed the tray is removed from the mouth and the slight retaining tongues that have formed are removed. The impression compound is so securely bonded to the impression tray that it can be removed from the impression tray again only by destruction. Attempts to then use the tray in the same manner for an adhesive charge with addition-crosslinking silicones are unsuccessful. The addition-crosslinking impression composition is easily lifted away from the impression tray.

While the invention has been described in conjunction with the specific embodiments outlined above, it is evident that many alternatives, modifications, and variations will be apparent to those skilled in the art. Accordingly, the preferred embodiments of the invention are intended to be illustrative and not limiting. Various changes may be made without departing from the spirit and scope of the invention as defined in the claims.

What is claimed:

1. An adhesive containing a copolymer comprising the following structural units:

(a) a unit corresponding to formula (I)

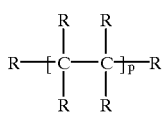

(I)

and (b) a unit corresponding to formula (II)

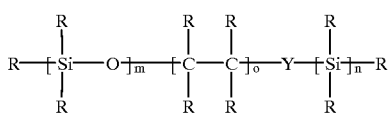

(II)

wherein m and p are each, independently of one another, selected from any whole number greater than zero; 1wherein n is 1;

wherein o is 1 or zero;
   wherein Y is either a bond or a group of the formula —CR'$_2$— or —CO—O—CR$_2$—CR$_2$—CR$_2$—;
   wherein each R radical, independently of one another, is selected from the group consisting of hydrogen, alkyls, groups of the formula —CR'$_2$—OR', —OR', —COOR', SiR$_c$R$_d$R$_e$, and —NR$_d$—R$_e$, organic acid, anhydride, a readily hydrolysable ester of the formula —O—CO—R$_c$, a readily hydrolysable amide of the formula —NR$_d$—CO—R$_c$, a phenyl group, a group of the formula —CR$_e$R$_f$CHR$_{g—SiX3}$, a group of the formula —SiOSiO(SiO)$_m$H, an epoxy group, an aziridine group, a phosphate, a phosphonate group or an anhydride thereof, and a bond, or wherein two R radicals together represent a group of the formula =CR$_2$;

wherein each of the radicals R',R$_c$, R$_d$, R$_e$, R$_f$, R$_g$ and X are, independently of one another, selected from the group consisting of hydrogen, —OH, alkyls, alkoxy groups and aryl groups;

with the proviso that in at least one unit of formula II, at least one of the R radicals bonded to a Si atom is selected from the group consisting of —OH, —OR$_c$, —NR$_d$R$_e$, —OCOR$_c$, and —NR$_d$COR$_e$.

2. An adhesive containing a copolymer according to claim 1, wherein the radicals R, R', R$_c$, R$_d$, R$_e$, R$_f$, R$_g$ and X are each, independently of one another, selected from the group consisting of hydrogen, —OH, methyl, ethyl, methoxy and ethoxy groups.

3. An adhesive containing a copolymer according to claim 1, wherein at least one unit corresponding to formula (I) and at least one unit corresponding to formula (II) are linked to one another by either C—Si bonds or —OCO— bonds.

4. An adhesive containing a copolymer according to claim 1, wherein the alkyl groups consist of 1 to 12 carbon atoms and are selected from the group consisting of substituted, unsubstituted, branched and unbranched alkyls.

5. An adhesive containing a copolymer according to claim 4, wherein the alkyl groups have from 1 to 6 carbon atoms.

6. An adhesive containing a copolymer according to claim 5, wherein the alkyl groups have from 1 to 3 carbon atoms.

7. An adhesive containing a copolymer according to claim 1, wherein the aryl groups are substituted or unsubstituted structures having from one to four condensed aromatic rings.

8. An adhesive containing a copolymer according to claim 1, wherein the ratio of the silanol-siloxane fragments of formula II to the fragments of formula I in the copolymer is at least 1:25.

9. An adhesive containing a copolymer according to claim 1, wherein the ratio of the silanol-siloxane fragments of formula II to the fragments of formula I in the copolymer is at least 1:10.

10. An adhesive containing a copolymer according to claim 1, wherein the ratio of the silanol-siloxane fragments of formula II to the fragments of formula I in the copolymer is at least 1:5.

11. A process for the preparation of a copolymer comprising the following steps:

a) copolymerizing unsaturated monomers, homopolymers thereof, copolymers thereof, or mixtures thereof, with SiH-group-containing monomers, SiH-group-containing homopolymers, Si-H-group containing copolymers, or mixtures thereof, and b) converting the Si-H groups into silanol groups or adding unsaturated silanol derivatives to the SiH groups.

12. A process according to claim 11, wherein the unsaturated compounds are copolymerised with SiH-group containing siloxanes and the SiH groups are converted into silanol groups or reactive derivatives thereof.

13. A process according to claim 11, wherein the unsaturated compounds are (co-) polymerised.

14. A process according to claim 11, wherein unsaturated compounds or compounds of the formula

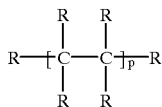

wherein p are each, independently of one another, selected from any whole number greater than zero; wherein each R radical, independently of one another, is selected from the group consisting of hydrogen, alkyls, groups of the formula —CR'$_2$—OR', —OR', —COOR', —SiR$_c$R$_d$R$_e$, and —NR$_d$—R$_c$, organic acid, anhydride, a readily hydrolysable ester of the formula —O—CO—R$_c$, a readily hydrolysable amide of the formula —NR$_d$—CO—R$_c$, a phenyl group, a group of the formula —CR$_e$,R$_f$CHR$_{g-SiX3}$, a group of the formula —SiOSiO(SiO)$_m$H, an epoxy group, an aziridine group, a phosphate, a phosphonate group or an anhydride thereof, and a bond, or wherein two R radicals together represent a group of the formula =CR$_2$; wherein each of the radicals R', R$_c$, R$_d$, R$_e$, R$_f$, R$_g$ and X are, independently of the one another, selected from the group consisting of hydrogen, —OH, alkyls, alkoxy groups and aryl groups; with the proviso that in at least one unit of formula II, at least one of the R radicals bonded to a Si atom is selected from the group consisting of —OH, —OR$_c$, —NR$_d$R$_c$, —OCOR$_c$ and —NR$_d$COR$_c$.

15. A process according to claim 11, wherein at least some of the SiH groups are converted into silanol groups or reactive derivatives thereof by hydrolysis, alcoholysis, acidolysis or similar reactions.

16. A process according to claim 11, wherein at least some of the silanol groups are bonded by adding to the SiH-group-containing siloxanes unsaturated compounds containing at least one silanol group or reactive derivatives thereof.

17. A process according to claim 11, wherein the unsaturated compounds are selected from the group consisting of (meth)acrylates, vinyl benzenes, vinyl ethers, allyl compounds, vinyl silanes, and mixtures thereof.

18. A process according to claim 11, wherein the unsaturated compounds are selected from the group consisting of mono (meth)acrylates, monovinyl benzenes, monovinyl ethers, monoallyl compounds, monovinyl silanes, and mixtures thereof.

19. A process according to claim 11, wherein the unsaturated compounds contain at least one additional functional group.

20. A process according to claim 19 wherein the additional functional groups is selected from the group consisting of hydrogen silyl, alkoxysilyl, epoxy, aziridine, carboxylic acid, carboxylic acid anhydride, phosphate, phosphonate, and anhydrides.

21. A composition comprising a condensation-crosslinking silicone system bonded to a partially soluble plastic component via an adhesive comprising a copolymer described in claim 1.

22. A composition comprising a condensation-crosslinking silicone bonded to a prosthesis material via an adhesive comprising a copolymer described in claim 1.

23. A composition comprising a condensation-crosslinking silicone impression material bonded to an impression tray via an adhesive comprising a copolymer described in claim 1.

24. An additive for crosslinking condensation-crosslinkable silicone materials comprising an adhesive comprising a copolymer described in claim 1.

25. A coating comprising a copolymer described in claim 1.

* * * * *